United States Patent
Guggenheim et al.

(10) Patent No.: US 7,153,394 B2
(45) Date of Patent: Dec. 26, 2006

(54) SYSTEM TO ISOLATE DIANHYDRIDES

(75) Inventors: Thomas Link Guggenheim, Mt. Vernon, IN (US); David Anthony Mongilio, Parkersburg, WV (US)

(73) Assignee: General Electric Company, Schenectady, NY (US)

( * ) Notice: Subject to any disclaimer, the term of this patent is extended or adjusted under 35 U.S.C. 154(b) by 13 days.

(21) Appl. No.: 10/250,270

(22) Filed: Jun. 19, 2003

(65) Prior Publication Data

US 2004/0015328 A1    Jan. 22, 2004

Related U.S. Application Data

(62) Division of application No. 10/063,795, filed on May 14, 2002, now Pat. No. 6,710,187.

(51) Int. Cl.
*B01D 3/06* (2006.01)
*B01D 3/28* (2006.01)
*B01D 5/00* (2006.01)
*B01D 11/00* (2006.01)

(52) U.S. Cl. ............. 202/168; 202/172; 202/186; 202/236; 159/2.1; 159/6.2; 159/13.2; 159/901

(58) Field of Classification Search ............ 202/172, 202/168, 186, 236; 203/87–89, 98; 159/2.1, 159/6.2, 13.2, 901; 549/241
See application file for complete search history.

(56) References Cited

U.S. PATENT DOCUMENTS

| 38,366 | A * | 5/1863 | Kenton ............... 208/184 |
| 4,318,857 | A | 3/1982 | Webb et al. ........... 260/346.3 |
| 4,329,291 | A | 5/1982 | Webb et al. ........... 549/241 |
| 4,329,292 | A | 5/1982 | Webb ................ 549/241 |
| 4,329,496 | A | 5/1982 | Webb ................ 562/468 |
| 4,340,545 | A | 7/1982 | Webb et al. ........... 549/241 |
| 4,517,298 | A * | 5/1985 | Tedder ............... 435/160 |
| 4,571,425 | A | 2/1986 | Silva ................ 549/241 |
| 4,584,388 | A | 4/1986 | Webb ................ 549/241 |
| 5,328,596 | A * | 7/1994 | Gammie, II .......... 208/321 |
| 5,658,433 | A * | 8/1997 | Baird ................ 202/153 |
| 5,756,780 | A * | 5/1998 | Ohyama et al. ....... 549/541 |
| 5,840,809 | A * | 11/1998 | Ohtsuka et al. ....... 525/316 |
| 6,187,965 | B1 * | 2/2001 | Bhatt et al. .......... 568/810 |
| 6,498,224 | B1 * | 12/2002 | Odle et al. ........... 528/170 |
| 6,710,187 | B1 * | 3/2004 | Guggenheim et al. .... 549/241 |

FOREIGN PATENT DOCUMENTS

DE        32 13 166 A1    10/1983
WO     WO 03/050165       6/2003

OTHER PUBLICATIONS

DE 3213166. Publication Date Oct. 13, 1983. Abstract Only (1 page).
European Search Report Dated Aug. 6, 2003.

* cited by examiner

*Primary Examiner*—Virginia Manoharan

(57) ABSTRACT

A process to isolate dianhydride from an exchange reaction comprises extracting a bisimide/anhydride exchange reaction aqueous phase with an organic solution comprising an exchange catalyst at a first temperature and pressure to form an extracted aqueous phase comprising water, exchange catalyst and a dianhydride precursor; removing water from the extracted aqueous phase at a second temperature and pressure to form a molten phase, wherein the second pressure is less than the first pressure; removing water and exchange catalyst from the molten phase at a third temperature and pressure to form an isolation mixture; and converting the dianhydride precursor in the isolation mixture to dianhydride at a fourth temperature and pressure, wherein the fourth temperature is greater than the second and third temperatures and the fourth pressure is less than the second and third pressures.

10 Claims, 1 Drawing Sheet

SYSTEM TO ISOLATE DIANHYDRIDES

CROSS REFERENCE TO RELATED APPLICATIONS

This application is a divisional of U.S. patent application Ser. No. 10/063,795 filed on May 14, 2002 now U.S. Pat. No. 6,710,187, which is incorporated by reference herein.

BACKGROUND OF INVENTION

The disclosure relates to the isolation of dianhydrides. In particular, the disclosure relates to the isolation of dianhydrides with low color.

Polymers such as polyetherimide are most desirably colorless or very light colored (have low color). Polyetherimide is typically produced by reacting dianhydrides with diamines. It is therefore desirable that the dianhydrides and diamines have low color in order to produce polyetherimide with low color.

SUMMARY OF INVENTION

A process to isolate dianhydride from an exchange reaction comprises extracting a bisimide/anhydride exchange reaction aqueous phase with an organic solution comprising an exchange catalyst at a first temperature and pressure to result in an extracted aqueous phase comprising water, exchange catalyst and a dianhydride precursor; removing water from the extracted aqueous phase at a second temperature and pressure to form a molten phase wherein the second pressure is less than the first pressure; removing water and exchange catalyst from the molten phase at a third temperature and pressure to form an isolation mixture; and converting the dianhydride precursor in the isolation mixture to dianhydride at a fourth temperature and pressure, wherein the fourth temperature is greater than the second and third temperatures and the fourth pressure is less than the second and third pressures.

In another aspect, a process to isolate dianhydride from an exchange reaction comprises extracting a bisimide/anhydride exchange reaction aqueous phase with an organic solution comprising an exchange catalyst at a first temperature and pressure to form an extracted aqueous phase comprising water, exchange catalyst and dianhydride precursor; feeding the extracted aqueous phase to a flash vessel operated at a second temperature and pressure to form a molten phase; feeding the molten phase to a falling film evaporator operated at a third temperature and pressure to produce an isolation mixture having an exchange catalyst to dianhydride precursor ratio of about 0.4 to about 0.8; converting the dianhydride precursor in the isolation mixture to dianhydride in a wiped film evaporator at a fourth temperature and pressure.

In another aspect, a system for dianhydride isolation comprises a flash vessel that receives an extracted aqueous phase from an extraction column and forms a molten phase, a falling film evaporator in fluid communication with a first outlet of the flash vessel, wherein the falling film evaporator receives the molten phase from the flash vessel and forms an isolation mixture; and a wiped film evaporator in fluid communication with a first outlet of the falling film evaporator, wherein the wiped film evaporator receives the isolation mixture from the falling film evaporator and comprises a first outlet for collection of the isolated dianhydride.

BRIEF DESCRIPTION OF THE DRAWINGS

The FIGURE is a schematic representation of a system for the isolation of dianhydride.

DETAILED DESCRIPTION

Figure 1:
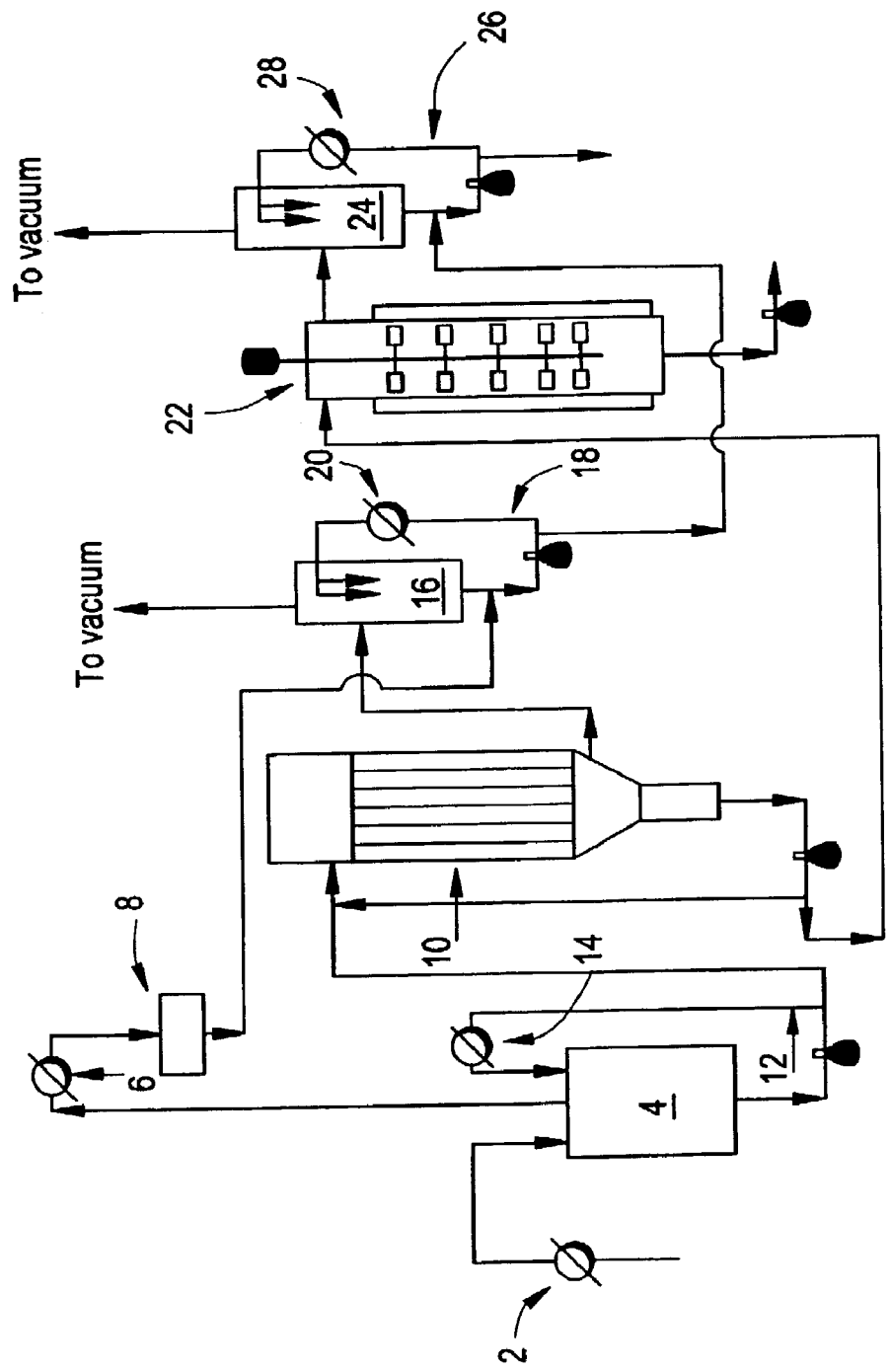

A process to isolate dianhydride from an exchange reaction comprises extracting a bisimide/anhydride exchange reaction aqueous phase with an organic solution comprising an exchange catalyst at a first temperature and pressure to form an extracted aqueous phase comprising water, exchange catalyst and dianhydride precursor. A majority of the water is then removed from the extracted aqueous phase at a second temperature and pressure to form a molten phase, preferably in a flash vessel. The molten phase is then subjected to reduced pressure (a vacuum) at a third temperature, preferably in a falling film evaporator, to remove catalyst, water and optionally residual starting materials, and form an isolation mixture. The dianhydride precursor in the isolation mixture is then converted to dianhydride at a fourth temperature under further reduced pressure, preferably in a wiped film evaporator. This process can be performed batchwise or in a continuous manner. Preferably the process is continuous.

The conditions of isolation of the dianhydride, namely the separation of the precursor from the exchange reaction and its subsequent conversion to dianhydride can have a significant effect on the color of the isolated dianhydride. Factors that contribute to the development of color in the dianhydride include the residence time of the dianhydride precursor(s) at elevated temperatures, in that long precursor residence times can result in highly colored dianhydride. Unexpectedly it has discovered by the inventors hereof that by reducing the amount of catalyst in the isolation mixture prior to converting the dianhydride precursor to dianhydride, dianhydride with significantly less color can be produced, even with increased residence time at elevated temperatures.

In another embodiment, the process to isolate dianhydride from an exchange reaction proceeds wholly or partially in the absence of air. The exposure of the catalyst to air in the presence of the dianhydride precursor at elevated temperatures can increase the color of the dianhydride. Without being bound by theory, it is thought that exposure of the exchange catalyst to air at elevated temperatures results in a reactive intermediate that, in turn, reacts with the dianhydride precursor or dianhydride to form highly colored impurities.

Dianhydrides are typically produced by the exchange reaction shown in Scheme I below. Molten bismide 1 is combined with phthalic anhydride 2 in the presence of water and an exchange catalyst. The exchange reaction produces phthalimide 3 and a precursor of the dianhydride such as the tetra acid salt 4.

Scheme 1

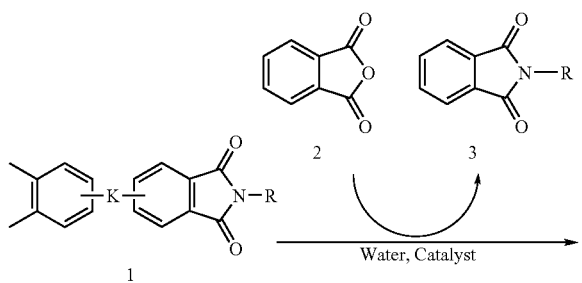

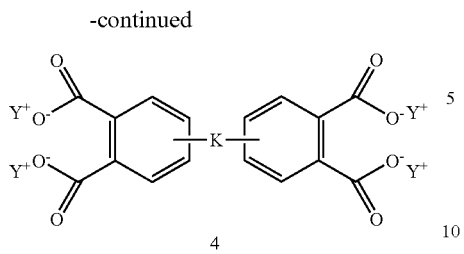

The dianhydride precursor is subsequently converted to dianhydride 5.

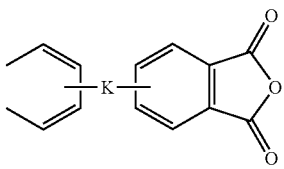

The divalent bonds of the —K— group are in the 3,3', 3,4', 4,3', or the 4,4' positions, and K includes O, S, $SO_2$ and O—W—O wherein W includes, but is not limited, to divalent radicals of formula (I).

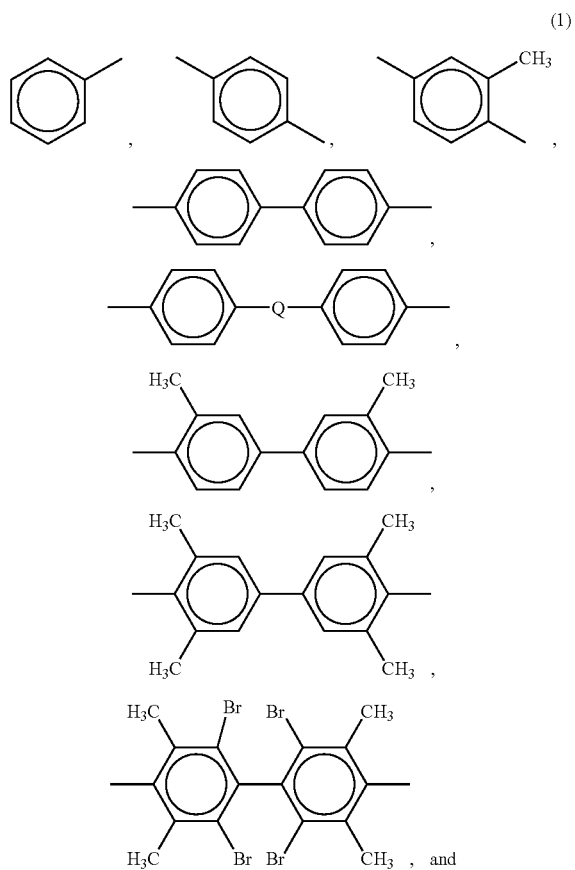

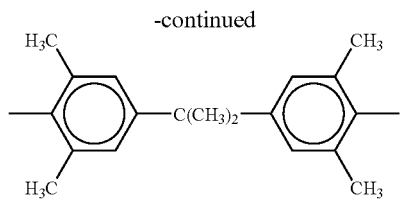

wherein Q includes but is not limited to a divalent moiety selected from the group consisting of —O—, —S—, —C(O)—, —SO$_2$—, —SO—, —C$_y$H$_{2y}$— (y being an integer from 1 to 5), and halogenated derivatives thereof, including perfluoroalkylene groups. A preferred dianhydride is 2,2-bis(4-(3,4-dicarboxyphenoxy)phenyl)propane dianhydride.

R is a monovalent organo radical selected from the group consisting of $C_{1-8}$ alkyl radicals and $C_{6-13}$ aromatic radicals. Y represents a positive ion, the identity of which is not particularly limited. Typically Y is the protonated form of the exchange catalyst.

Exchange catalysts include, but are not limited to, $C_{1-20}$ trialkylamines. A preferred exchange catalyst is triethylamine. The exchange catalyst used in the exchange reaction as described above and the exchange catalyst present in the extraction column may be the same trialkylamine or different trialkylamines. Preferably they are the same.

In the exchange reaction molten bisimide is typically combined with about 3 to about 8 molar excess of molten anhydride in the presence of about 60 to about 80 weight percent (wt %) water based on the total weight of the reaction mixture water and about 0.5 to about 15 mole percent (mol %) of exchange catalyst with respect to anhydride at about 150 to about 210° C. The exchange reaction is agitated for about 0.5 to about 3 hours. It has been observed that when the exchange reaction is run in a liquid full reactor and the reactants are added to the top of the reactor, a layer comprising mostly exchange catalyst can form. Formation of the exchange catalyst layer effectively removes catalyst from the reaction, causing a significant decrease in the production of dianhydride precursor. It is therefore preferable for the reactants to be added to the bottom of the reactor. When the reactants are added to the bottom of the reactor, no exchange catalyst layer forms and all of the exchange catalyst is available to participate in the reaction.

The precursor of the dianhydride resulting from the exchange reaction is resident in the aqueous phase. As will be appreciated by one of ordinary skill in the art, one dianhydride precursor is a tetra acid and may be present as such, or any number of the acid groups may be deprotonated and present in salt form. It is believed that a mixture of protonated and deprotonated species is present in the aqueous phase. The aqueous phase may also contain phthalic anhydride in salt form.

The aqueous phase resulting from the exchange reaction is extracted with an organic solution containing an exchange catalyst, preferably in an extraction column. The aqueous phase is contacted with the organic solution for about 1 to about 3, preferably about 1 to about 2, and more preferably about 1 to about 1.5 hours. The catalyst is present in the organic solution to convert any exchange reaction intermediate products to dianhydride precursor. Extraction preferably occurs at first temperature of about 135 to about 190° C. and a first pressure of about 3,000 to about 17,000 torr, preferably about 10,000 to about 12,000 torr, to facilitate the conversion of intermediates. The organic solution typically contains about 1 to about 7, preferably about 2 to about 5 and more preferably about 3 to about 4 wt % catalyst, based on the total weight of the organic solution. Suitable organic solvents for use in the organic solution include, but are not limited to, alkyl benzenes with alkyl groups having from 1 to 5 carbons, benzene, and halogenated aromatics. When using an extraction column, the aqueous phase from the exchange reaction is typically fed into the top of the extraction column while the organic solution is fed into the bottom of the exchange column.

After extraction the aqueous phase is subjected to a second temperature and pressure to remove water, preferably in a flash vessel, to form a molten phase, typically for about 60 to about 120 minutes. Useful pressures are less than about 1050, preferably less than about 850 and more preferably less than or equal to about 800 torr but greater than or equal to about 300 torr. The second pressure is less than the first pressure. Useful temperatures are about 100 to about 180, preferably about 140 to about 160, and more preferably about 145 to about 155° C. After removal the water may then be condensed. The condensed water may then be chilled and used in the condensers associated with later water and/or catalyst removal as described below or recycled back to the exchange reaction.

The molten phase is subjected to a third temperature and pressure for about 5 to about 30 minutes to remove catalyst, additional water and optionally residual starting materials such as phthalic anhydride to form an isolation mixture that has a catalyst to dianhydride precursor ratio of about 0.4 to about 0.8, preferably about 0.5 to about 0.7 and more preferably about 0.6 to about 0.65. Useful temperatures are less than about 260, preferably less than about 220 and more preferably less than about 200° C. Additionally, the temperature is greater than about 150, preferably greater than about 170 and more preferably greater than about 180° C. Useful pressures are less than about 400, preferably less than about 200 and more preferably less than about 150 torr. The pressure is greater than about 30, preferably greater than about 50 and more preferably greater than about 100 torr.

In a preferred embodiment, the molten phase is fed to a falling film evaporator. As readily understood by one of ordinary skill in the art, the number of tubes, the length of the tubes and the diameter of the tubes contained in the falling film evaporator determines the overall surface area for the formation of the film and hence relates to the rate at which the volatile materials are removed, primarily residual water, catalyst and optionally residual starting materials such as phthalic anhydride. It is well within the skill of one with ordinary skill in the art to match the surface area of the falling film evaporator to the desired flow rate of the process stream in a continuous process and to the desired extent of water and catalyst removal. The volatile materials are preferably taken overhead to a condenser, such as a chilled spray condenser, wherein the volatile material is condensed through the use of a chilled spray. When the condensed material contains phthalic anhydride it is typically present in salt form. The condensed material itself may then be chilled in a heat exchanger and used as the spray in the same spray condenser, another spray condenser or recycled for use in the exchange reaction.

The falling film evaporator is maintained at a reduced pressure of less than about 400, preferably less than about 200 and more preferably less than about 150 torr. The pressure of the falling film evaporator is greater than about 30, preferably greater than about 50 and more preferably greater than about 100 torr. The temperature of the oil heating the tubes of the falling film evaporator is less than about 260, preferably less than about 220 and more preferably less than about 200° C. Additionally, the temperature of the oil in the falling film evaporator tubes is greater than about 150, preferably greater than about 170 and more preferably greater than about 180° C. The temperature of the falling film evaporator is preferably less than the temperature of the wiped film evaporator.

The isolation mixture is subjected to a fourth temperature and pressure for typically about 5 to about 30 minutes to convert the dianhydride precursor to dianhydride. The amount of time as well as the temperature is generally dependent upon the identity of the dianhydride and is readily determined by one of ordinary skill in the art. Generally, useful temperatures are less than about 350, preferably less than about 310 and more preferably less than about 295° C. The fourth temperature is typically greater than about 250, more preferably greater than about 270, and most preferably greater than about 275° C. Useful pressures are less than about 50, preferably less than about 30 and more preferably less than about 25 torr. The fourth pressure is greater than about 5, preferably greater than about 10 and more preferably greater than about 20 torr. The conversion of the dianhydride precursors to dianhydride is a cyclization with the concurrent formation of water. Advantageously, trace water, catalyst, and other residual volatile materials such as phthalic anhydride are also removed as vapor under the conditions required for conversion.

In a preferred embodiment, the conversion of the dianhydride precursor proceeds in a wiped film evaporator. The oil temperature of the wiped film evaporator is maintained at a temperature less than about 350, preferably less than about 310 and more preferably less than about 295° C. The oil temperature of the wiped film evaporator is greater than about 250, more preferably greater than about 270, and most preferably greater than about 275° C. The wiped film evaporator is maintained at a reduced pressure of less than about 50, preferably less than about 30 and more preferably less than about 25 torr. The pressure of the wiped film evaporator is greater than about 5, greater than about 10 and more preferably greater than about 20 torr.

The volatile materials removed in the wiped film evaporator are taken to a chilled spray condenser operated in a manner similar to that described above for the chilled spray condenser associated with the falling film evaporator. Material condensed in the spray condenser associated with the falling film evaporator may be chilled and used in the spray condenser associated with the wiped film evaporator.

Use of the above described process results in dianhydride with low color. Color may be quantified by the yellowness index as determined according to ASTM D1925. Dianhydride produced by the above described method, on a commercial scale, has a yellowness index of about 5 to about 8 with an average of about 6, a decrease of about 3 units when compared to dianhydride produced by prior art methods. Without being bound by theory, it is believed that the reduction of the yellowness index results from the removal of a greater amount of exchange catalyst from the precursor containing mixture before exposure to the high temperatures of the wiped film evaporator than has previously been possible. The dianhydride isolated using the above-described process has a catalyst content of less than about 50, preferably less than about 35 and more preferably less than about 20 parts per million (ppm). In contrast, dianhydride isolated by prior art methods has an average triethylamine content of about 50 to about 100 ppm and the triethylamine content is difficult to control.

The FIGURE is a schematic representation of a system for the isolation of dianhydride. In the FIGURE, the extracted aqueous phase from the extraction column is passed through heat exchanger 2 and fed to flash vessel 4. In flash vessel 4 water and optionally some exchange catalyst are removed as a vapor, affording a molten product phase comprising dianhydride precursor. The water vapor from flash vessel 4 is received by condenser 6 where it is condensed into water and collected in an accumulator 8. Flash vessel 4 is in fluid connection with falling film evaporator 10 which receives the molten phase from flash vessel 4. Flash vessel 4 may optionally have a recycle stream 12 that is fed through a heat exchanger 14 before returning to the flash vessel. In falling film evaporator 10 exchange catalyst, further water and optionally phthalic anhydride are removed as vapor to form an isolation mixture. The exchange catalyst and water vapor mixture is received by chilled spray condenser 16 where it is condensed to a liquid phase that is optionally recycled via recycle stream 18. The optional recycle stream 18 passes through chiller 20. Wiped film evaporator 22 is in fluid communication with falling film evaporator 10 and receives the isolation mixture. The isolation mixture comprises dianhydride precursors which are converted to dianhydride in the wiped film evaporator 22. Trace water, some residual exchange catalyst as well as other residual volatile materials are removed as a vapor from the isolation mixture in the wiped film evaporator. The vapor from the wiped film evaporator is received by chilled spray condenser 24, which is in fluid communication with the wiped film evaporator. Chilled spray condenser 24 condenses the vapor from the wiped film evaporator to a liquid phase which may be recycled to the chilled spray condenser via recycle stream 26 that passes through chiller 28 or employed in the bisimide/anhydride exchange reaction. Dianhydride is collected from an outlet in the wiped film evaporator.

The invention is further illustrated by the following non-limiting examples.

EXAMPLES

Laboratory studies were conducted to simulate the isolation of dianhydride with flash vessel and wiped film evaporator as well as a flash vessel, falling film evaporator and wiped film evaporator. The laboratory set up constituted a flask placed in a gas chromatography oven. The flask was attached to a glass dual bulb Kugelrohr type extension located outside the GC oven by a glass extension piece. The dual bulb was attached to a Kugelrohr oscillating drive and a vacuum pump. The dual bulb was cooled by a dry ice/methylene chloride bath.

The flask was charged with aqueous effluent from the plant aqueous extraction column and a slight vacuum was applied to the flask as the flask was oscillated. The vacuum was lowered slowly until a full vacuum was obtained (about 0.5 torr or less). Once a full vacuum was established one of two temperature programs were initiated in the gas chromatography oven. Program A simulated an isolation process employing a flash vessel and a wiped film evaporator (control). Program B simulated an isolation process employing a flash vessel, falling film evaporator and wiped film evaporator. At the conclusion of each temperature program the oven door was opened and the flask was allowed to cool while still oscillating. The dianhydride, 2,2-bis(4-(3,4-dicarboxyphenoxy)phenyl)propane dianhydride, was removed from the flask and tested for yellowness according to ASTM D1925. Results from duplicate runs are shown in Table 1.

| Experiment No. | Temperature/Time Program | Yellowness Index |
|---|---|---|
| 1* | A | 7.64 |
| 2* | A | 7.76 |
| 3* | A | 8.54 |
| 4* | A | 7.87 |
| 5* | A | 7.54 |
| 6* | A | 7.92 |
| 7* | A | 8.79 |
| 8* | A | 8.04 |
| std dev = | | 0.41 |
| mean = | | 8.01 |
| 9 | B | 7.64 |
| 10 | B | 7.26 |
| 11 | B | 7.47 |
| std dev = | | 0.19 |
| mean = | | 7.46 |

*control

Following laboratory experimentation, a falling film evaporator was installed in the plant and operated as described above for the preferred embodiments. The average yellowness index of the isolated dianhydride decreased 3 units after installation of the falling film evaporator in the plant. The larger decrease in the yellowness index of the dianhydride produced in the plant when compared to the yellowness index of the dianhydride produced in the lab can be ascribed to the decreased incidence of air in the plant compared to the laboratory conditions.

While preferred embodiments have been shown and described, various modifications and substitutions may be made thereto without departing from the spirit and scope of the invention. Accordingly, it is to be understood that the present invention has been described by way of illustration and not limitations.

The invention claimed is:

1. A system for dianhydride isolation comprising
   an extraction column operated at a first temperature and pressure sufficient to form an extracted aqueous phase comprising water, exchange catalyst and dianhydride precursor;
   a flash vessel that receives the extracted aqueous phase from the extraction column and forms a molten phase wherein the flash vessel is operated at a second temperature and pressure sufficient to produce a molten phase;
   a falling film evaporator in fluid communication with a first outlet of the flash vessel, wherein the falling film evaporator receives the molten phase from the flash vessel and the falling film evaporator is operated at a third temperature and pressure sufficient to form an isolation mixture having an exchange catalyst to dianhydride precursor ratio of about 0.4 to about 0.8; and
   a wiped film evaporator in fluid communication with a first outlet of the falling film evaporator and operated at a fourth temperature and pressure wherein the wiped film evaporator receives the isolation mixture from the falling film evaporator and further wherein the wiped film evaporator comprises a first outlet for collection of isolated dianhydride and further falling film evaporator is operated at a temperature less than the temperature of the wiped film evaporator.

2. The system of claim 1, wherein the system further comprises a first heat exchanger disposed at an inlet of the flash vessel.

3. The system of claim 1, wherein the system further comprises a condenser disposed at a second outlet of the flash vessel that receives an aqueous phase from the flash vessel.

4. The system of claim 1, further comprising a recycle stream at the flash vessel wherein the recycle stream flows through a second heat exchanger.

5. The system of claim 1, further comprising a recycle stream at the falling film evaporator.

6. The system of claim 1, further comprising a first chilled spray condenser disposed at a second outlet of said falling film evaporator.

7. The system of claim 6, wherein the first chilled spray condenser receives and utilizes condensate recycled from the first chilled spray condenser.

8. The system of claim 6, further comprising a second chilled spray condenser disposed at a second outlet of the wiped film evaporator wherein the second chilled spray condenser receives and utilizes condensate from the first chilled spray condenser.

9. The system of claim 1, further comprising a second chilled spray condenser disposed at a second outlet of the wiped film evaporator.

10. The system of claim 1, wherein the system is operated wholly or partially in the absence of air.

* * * * *